US005762961A

United States Patent [19]
Roser et al.

[11] Patent Number: 5,762,961
[45] Date of Patent: Jun. 9, 1998

[54] RAPIDLY SOLUBLE ORAL SOLID DOSAGE FORMS, METHODS OF MAKING SAME, AND COMPOSITIONS THEREOF

[75] Inventors: Bruce J. Roser, Cambridge; Julian Blair, St. Ives, both of United Kingdom

[73] Assignee: Quadrant Holdings Cambridge Ltd., Cambridge, England

[21] Appl. No.: 599,277

[22] Filed: Feb. 9, 1996

[51] Int. Cl.$^6$ ............................... A61K 9/20; A61K 9/22
[52] U.S. Cl. .................... 424/464; 424/465; 424/468; 424/489
[58] Field of Search .................... 424/465, 464, 424/489, 468

[56] References Cited

U.S. PATENT DOCUMENTS

| | | |
|---|---|---|
| 3,557,717 | 1/1971 | Chivers . |
| 3,619,294 | 11/1971 | Black et al. . |
| 3,632,357 | 1/1972 | Childs . |
| 3,655,442 | 4/1972 | Schwer et al. . |
| 4,127,502 | 11/1978 | Li Mutti et al. . |
| 4,158,544 | 6/1979 | Louderback . |
| 4,327,076 | 4/1982 | Puglia et al. . |
| 4,327,077 | 4/1982 | Puglia et al. ............................ 424/38 |
| 4,588,744 | 5/1986 | McHugh . |
| 4,678,812 | 7/1987 | Bollin, Jr. et al. . |
| 4,701,417 | 10/1987 | Portenhauser et al. . |
| 4,762,857 | 8/1988 | Bollin, Jr. et al. ...................... 514/777 |
| 4,865,871 | 9/1989 | Livesey et al. . |
| 4,883,762 | 11/1989 | Hoskins . |
| 4,891,319 | 1/1990 | Roser . |
| 5,026,566 | 6/1991 | Roser . |
| 5,112,616 | 5/1992 | McCarty ................................ 424/434 |
| 5,149,653 | 9/1992 | Roser . |
| 5,290,765 | 3/1994 | Wettlaufer et al. . |
| 5,306,506 | 4/1994 | Zema et al. ........................... 424/466 |
| 5,348,852 | 9/1994 | Bonderman . |
| 5,422,384 | 6/1995 | Samuels et al. . |
| 5,425,951 | 6/1995 | Goodrich, Jr. et al. .............. 424/520 |
| 5,466,470 | 11/1995 | Lajoie .................................... 424/641 |
| 5,482,720 | 1/1996 | Murphy et al. ....................... 424/489 |
| 5,501,861 | 3/1996 | Makino et al. ....................... 424/464 |
| 5,512,547 | 4/1996 | Johnson et al. ....................... 514/21 |
| 5,589,167 | 12/1996 | Cleland et al. ...................... 424/85.7 |

FOREIGN PATENT DOCUMENTS

| | | |
|---|---|---|
| 0415567 | 3/1991 | European Pat. Off. . |
| 606 753 | 7/1994 | European Pat. Off. . |
| 636 693 | 2/1995 | European Pat. Off. . |
| 0714905 | 6/1996 | European Pat. Off. . |
| 58-216695 | 12/1983 | Japan . |
| 9977 | 6/1844 | United Kingdom . |
| 1 381 588 | 1/1975 | United Kingdom . |
| 1381588 | 1/1975 | United Kingdom . |
| 2206273 | 1/1989 | United Kingdom . |
| 87/00196 | 1/1987 | WIPO . |
| WO 87/00196 | 1/1987 | WIPO . |
| WO 89/06542 | 7/1989 | WIPO . |
| WO 92/02133 | 2/1992 | WIPO . |
| WO 93/02834 | 2/1993 | WIPO . |
| 93/10758 | 6/1993 | WIPO . |
| 93/11220 | 6/1993 | WIPO . |
| 95/06126 | 3/1995 | WIPO . |
| WO 95/33488 | 12/1995 | WIPO . |

OTHER PUBLICATIONS

Dialog® English Abstract of JP 58–216695 (Dec. 16, 1983).
Dialog® WPI File 351 Abstract of PCT WO 87/05300 (Sep. 11, 1987).
Sakurai, Y (ed.), "Food General Dictionary" Sixth Edition (The English translation is 10 pages total.).
Kanna et al., "Denaturation of Fish Muscle Protein by Dehydration–V," *Bull. Tokai Reg. Fish. Res. Lab.* (1974) 77:1–14.
Reasons for Opposition, (1995) 5 pages total.
Supplement of Reasons for Opposition (Dec. 31, 1995), 23 pages total.
Grounds for Rejection, (1995) 6 pages total.
Handbook of Natural Materials for Food Processing, Ninth Edition (Translation to be disclosed at a later date).
Chemical Dictionary, $7^{th}$ Edition (Translation to be disclosed at a later date).
*Stability and characterization of protein and peptide drugs,* Wang et al. (eds.), 1993, table of contents enclosed herewith.
Pogany et al., "A new approach to the theory of tabletting" *Acta Pharm. Hung.* (1988) 58:49–55.
Doelker, "Recent advances in tableting science" *Boll. Chim. Farm.* (1988) 127:37–49.
Hiestand et al., "Physical processes of tableting" *J. Pharm. Sci.* (1977) 66:510–519.
Cooper et al., "Tableting research and technology" *J. Pharm. Sci.* (1972) 61:1511–1555.
Rudnic et al., "Oral solid doseage forms" Chapter 92, *Remington: The Science and Practice of Pharmacy,* Nineteenth Edition, Gennaro Ed. (1995) Mack Publishing Company, Pennsylvania vol. II, pp. 1615–1649.
Niwa et al., "Preparation of agglomerated crystals for direct tabletting and microencapsulation by the spherical crystallization technique with a continuous system" *Pharm. Res.* (1994) 11:478–484.
Franz et al., "Cost evaluation of alternative pharmaceutical tableting processes by simulation" *J. Pharm. Sci.* (1980) 69:621–628.

(List continued on next page.)

*Primary Examiner*—Thurman K. Page
*Assistant Examiner*—Sharon Howard
*Attorney, Agent, or Firm*—Susan K. Lehnhardt

[57] ABSTRACT

The invention provides methods of making rapidly soluble tablets of decreased weight compared to similar solid tablets. The invention further provides novel, rapidly soluble tablets of decreased weight compared to similar solid tablets. The tablets offer increased rates of dissolution and disintegration.

12 Claims, No Drawings

OTHER PUBLICATIONS

Lipps et al., "Characterization of wet granulation process parameters using response surface methodology. 1. Top-spray fluidized bed" *J. Pharm. Sci.* (1994) 83:937–947.

Drissi–Alami et al., "The effects of the tabletting machine speed on physical characteristics of pharmaceutical powers" *J. Pharm. Belg.* (1993) 48:43–52.

Ishino et al., "Influence of tabletting speed on compactibility and compressibility of two direct compressible powders under high speed compression" *Chem. Pharm. Bull.* (1990) 38:1987–1992.

Sendall et al., "A study of powder adhesion to metal surfaces during compression of effervescent pharmaceutical tablets" *J. Pharm. Pharmacol.* (1986) 38:489–493.

Jetzer, "Measurement of hardness and strength of tablets and their relation to compaction performance of powders" *J. Pharm. Pharmacol.* (1986) 38:254–258.

Reading et al., "The effects of binder film characteristics on granule and tablet properties" *J. Pharm. Pharmacol.* (198) 36:421–426.

Paronen et al., "Compressional characteristics of four starches" *J. Pharm. Pharmacol.* (1983) 35:627–635.

Nakagawa, "Effects of tableting procedures on the preferred orientation of crystalline particles" *Chem. Pharm. Bull.* (1982) 30:1401–1407.

Elsabbagh et al., "Physical properties and dissolution profiles of acetaminophen and acetylsalicyclic acid tables made from sucrosebased vehicles" *Pharmazie* (1981) 36:488–492.

Naito et al., "Prediction of tableting problems such as capping and sticking: Theoretical calculations" *J. Pharm. Sci.* (1977) 66:254–259.

Healey et al., "The mechanical properties of some binders used in tableting" *J. Pharm. Pharmac.* (1974) 26 Suppl:41P–46P.

York et al., "The effect of temperature on the mechanical properties of some pharmaceutical powders in relation to tableting" *J. Pharm. Pharmac.* (1972) 24 Suppl:47P–56P.

Sebhatu et al. "Effect of moisture sorption on tabletting characteristics of spray dried (15% amorphous) lactose" *Pharm. Res.* (1994) 11:1233–1238.

Vromans et al., "Studies on tabletting properties of lactose. Part 1. The effect of intial particle size on binding properties and dehydration characteristics of lactose" *Acta Pharm. Suec.* (1985) 22:163–172.

Vromans et al., "Studies on tableting properties of lactose. Part 2. Consolidation and compaction of different types of crystalline lactose" *Pharm. Weekbl [Sci]* (1985) 7:186–193.

De Boer et al., "Studies on tableting properties of lactose. Part III. The consolidation behaviour of sieve fractions of crystalline α–lactose monohydrate" *Pharm Weekbl [Sci]* (1986) 8:145–150.

Van Kamp et al., "Studies on tableting properties of lactose. V. Effects of both lubrication and addition of disintegrants on properties of tablets prepared from different types of crystalline lactose" *Acta Pharm. Suec.* (1986) 23:217–230.

Vromans et al., "Studies on tableting properties of lactose. VI. Consolidation and compaction of spray dried amorphous lactose" *Acta Pharm. Suec.* (1986) 23:231–240.

Georgakopoulos et al., "The effects of using different grades of PVP and gelatin as binders in the fluidized bed granulation and tableting of lactose" *Pharmazie* (1983) 38:240–243.

York et al., "Science Papers. The tensile strength and compression behaviour of lactose, four fatty acids, and their mixtures in relation to tableting" *J. Pharm. Pharmac.* (1973) 25:Suppl:1P–11P.

Blakely et al., "Dry instant blood typing plate for bedside use" *Lancet* (1990) 336:854–855.

Roser, "Trehalose, a new approach to premium dried foods" *Trends in Food Sci. and Tech.* (Jul. 1991) pp. 166–169.

Colaco et al., "Trehalose stabilisation of biological molecules" *Biotechnol. Internat.* (1992) pp. 345–350.

Roser, "Trehalose dyring: A novel replacement of freeze–drying" *BioPharm.* (1991) 4:47–53.

Colaco et al., "Extraordinary stability of enzymes dried in trehalose: Simplified molecular biology" *BioTech.* (1992) 10:1007–1011.

Roser et al., "A sweeter way to fresher food" *New Scientist* (May 1993) pp. 25–28.

Madžarovová–Nohejlova, "Trehalase deficiency in a family" *Gastroenterol.* (1973) 65:130–133.

RAPIDLY SOLUBLE ORAL SOLID DOSAGE FORMS, METHODS OF MAKING SAME, AND COMPOSITIONS THEREOF

DESCRIPTION

1. Technical Field

This invention relates to the making of porous, rapidly soluble tablets. Compositions in tablet form are also encompassed by the invention. The invention also encompasses methods of making the rapidly soluble tablets using various forms of trehalose dihydrate, amorphous trehalose and anhydrous trehalose and mixtures thereof.

2. Background

Drugs and other active agents are most frequently administered orally by means of solid dosage forms such as tablets and capsules. Large scale production methods used for their preparation usually require that they contain other materials in addition to the active ingredients. Additives may also be included in the formulations to facilitate handling, enhance the physical appearance, improve stability and aid in delivery of the drug to the bloodstream after administration.

Tablets are defined as solid pharmaceutical dosage forms containing drug substances with or without suitable diluents. Typically, each tablet contains a single dose of an effective amount of the pharmaceutical agent. Tablets are prepared by compression, extrusion or molding methods. Tablets are popular as a dosage form because of the advantages afforded both to the manufacturer (e.g., simplicity and economy of preparation, stability and convenience in packaging, shipping and dispensing) and the patient (e.g., accuracy of dosage, compactness, portability, blandness of taste and ease of administration). Tablets are the most common form of solid dose drug delivery. For review see, Pogany et al. (1988) Acta Pharm. Hung. 58:49–55; Doelker et al. (1988) Boll. Chim. Farm. 127:37–49; Hiestand et al. (1977) J. Pharm. Sci. 66:510–519; and Cooper et al. (1972) J. Pharm. Sci. 61:1511–1555.

Compressed tablets are usually prepared by large-scale production methods, while molded tablets generally involve small-scale operations. Compressed tablets usually contain no special coating and are made from a small number of powdered, crystalline or granular materials or "diluents," alone or in combination with disintegrants, controlled-release polymers, lubricants, diluents and, in many cases, colorants.

Compressed tablets may be coated with a variety of substances which may alter their physical characteristics. Sugar coated tablets contain a sugar coating which may be colored. Such coatings are beneficial in masking drugs possessing objectionable tastes or odors and in protecting materials sensitive to humidity, light or oxidation. Film-coated tablets are covered with a thin layer or film of water soluble or insoluble material. A number of polymeric substances with film forming properties can be used. Film coating imparts the same general characteristics as sugar coating with a much shorter period required for coating. Enteric coated tablets are coated with substances that resist dissolution in gastric fluid but disintegrate in the intestine. Enteric coatings are useful for tablets containing drugs that are inactivated or destroyed in the stomach, for those which irritate the mucosa or as a means of delayed release of the medication. Multiple compressed tablets are those made by more than one compression cycle. These include, layered tablets and press-coated tablets. Compressed tablets can be formulated into controlled-release tablets which release drug over a prolonged period of time to provide pulsatile or sustained release.

Compressed tablets can also be formed into tablets for purposes other than oral delivery. These include, but are not limited to, disintegration into solution, effervescent tablets, compressed suppositories or inserts, and buccal and sublingual tablets. Compressed tablets for preparing solutions include, for instance, Halzone Tablets for Solution and Potassium Permanganate Tablets for Solution. Effervescent tablets contain sodium bicarbonate and an organic acid such as tartaric or citric in addition to the drug. In the presence of water, these additives react to liberate carbon dioxide which acts as a disintegrator and provides effervescence. Sufficient acid is added to produce a neutral or slightly acidic reaction when disintegration in water is rapid and complete. One drawback to the use of the effervescent type of disintegrator is that such tablets must be kept in a dry atmosphere at all times during manufacture, storage and packaging. Occasionally, vaginal suppositories, such as Metronidazole Tablets, are prepared by compression. Tablets for this use usually contain lactose as the diluent. Buccal and sublingual tablets are small, flat, oval tablets administered by insertion under the tongue or into the space between the cheek and gum where they dissolve slowly or erode; therefore, they are formulated and compressed with sufficient pressure to give a hard tablet. Progesterone or testosterone tablets may be administered in this manner.

There are a variety of methods of making compressed tablets. See, e.g., Remington: The Science and Practice of Pharmacy, Nineteenth Edition, Gennaro Ed. (1995) Vol. 11 pp. 1615–1649; Niwa et al. (1994) Pharm. Res. 11:478–484; and Franz et al. (1980) J. Pharm. Sci. 69:621–628. Interestingly, little has changed since the basic tableting method described in 1843, British Patent No. 9977. A number of parameters must be taken into account in tablet formulation such as moisture content and the physical characteristics of the substituents. This makes tablet formulation somewhat empirical. See, e.g., Lipps et al. (1994) J. Pharm. Sci. 83:937–947; Drissi-Alami et al. (1993) J. Pharm. Belg. 48:43–52; Ishino et al. (1990) Chem. Pharm. Bull. (Tokyo) 38:1987–1992; Sendall et al. (1986) J. Pharm. Pharmacol. 38:489–493; Fetzer et al. (1986) J. Pharm. Pharmacol. 38:254–258; Reading et al. (1984) J. Pharm. Pharmacol. 36:421–426; Paronen et al. (1983) J. Pharm. Pharmacol. 35:627–635; Nakagawa et al. (1982) Chem. Pharm. Bull. (Tokyo) 30:1401–1407; Elsabbagh et al. (1981) Pharmazie 36:488–492; Naito et al. (1977) J. Pharm. Sci. 66:254–259; Healey et al (1974) J. Pharm. Pharmacol. 26 Suppl: 41P–46P; and York et al. (1972) J. Pharm. Pharmacol. 24 Suppl:47P–56P.

A number of diluents are used in tableting to increase the bulk of the tablet to a practical size for compression. Diluents commonly used for this purpose include dicalcium phosphate dihydrate, tricalcium phosphate, calcium sulfate, lactose, spray-dried lactose, pregelatinized starch, microcrystalline cellulose, cellulose, kaolin, mannitol, sodium chloride, dry starch and powdered sugar. Certain diluents, particularly mannitol, lactose, sorbitol, sucrose and inositol, are used to make chewable tablets. Sucrose and mannitol are most frequently used in chewable tablets (AmStar and ICI Americas, respectively). Microcrystalline cellulose (Avicell, FMC) is a nonfibrous form of cellulose obtained by spray-drying washed, acid-treated cellulose and is available in several grades that range in average particle size from 20–100 μm. Certain drawbacks are inherent in the use of any diluent and they must be chosen based on their intended use and reactivity with the drug. For instance, the combination of amine bases or amine salts with lactose in the presence of an alkaline lubricant, results in losses in the bioavailaibility of the active agent and tablets that discolor on aging.

The superior tableting properties of lactose have, however, resulted in its widespread use and intensive study as a tableting excipient. Sebhatu et al. (1994) Pharm. Res. 11:1233–1238; Vromans et al. (1985) Acta Pharm. Suec. 22:163–172; Vromans et al. (1985) Pharm Weekbl [Sci] 7:186–193; De Boer et al. (1986) Pharm Weekbl [Sci] 8:145–150; Van Kamp et al. (1986) Acta Pharm. Suec. 23:217–230; Vromans et al. (1986) Acta Pharm. Suec. 23:231–241; Georgakopoulos et al. (1983) 38:240–243; and York et al. (1973) J. Pharm. Pharmacol. 25:Suppl:1P–11P. Hydrous lactose does not flow and its use is limited to tablet formulations prepared by the wet granulation method. Both anhydrous lactose and spray-dried lactose have good flowability and compressibility and can be used in direct compression provided a suitable disintegrant and lubricant are present in the tablet. Other constraints to the use of lactose in tableting are discussed below.

Agents used to impart cohesive qualities to the powdered material are referred to as binders or granulators. They impart a cohesiveness to the tablet formulation which insures the tablet remaining intact after compression, as well as improving the free-flowing qualities by the formulation of granules of desired hardness and size.

Trehalose, (α-D-glucopyranosyl-α-D-glucopyranoside), is a naturally occurring, non-reducing disaccharide which was initially found to be associated with the prevention of desiccation damage in certain plants and animals which can dry out without damage and can revive when rehydrated. Trehalose is available commercially in the dihydrate form, having a 8–10% water content. Trehalose has been shown to be useful in preventing denaturation of proteins, viruses and foodstuffs during desiccation. See U.S. Pat. Nos. 4,891,319; 5,149,653; 5,026,566; Blakeley et al. (1990) Lancet 336:854–855; Roser (July 1991) Trends in Food Sci. and Tech. 166–169; Colaco et al. (1992) Biotechnol. Internat. 345–350; Roser (1991) BioPharm. 4:47–53; Colaco et al. (1992) Bio/Tech. 10:1007–1011; and Roser et al. (May 1993) New Scientist, pp. 25–28. Trehalose dihydrate is available in good manufacturing process (GMP) grade crystalline formulations. A method of making a desiccant, anhydrous form of trehalose is described in EP patent publication no. 600 730. This method involves heating a trehalose syrup in the presence of a seed crystal and recovering the anhydrous trehalose.

Trehalose is found extensively in such diverse animal and plant species as bacteria, yeast, fungi, insects and invertebrates. In many insects, it is the major blood sugar. The only major source for man is dietary in foods such as mushrooms and yeast products. Madsarovova-Nohejlova (1973) Gastroenterol. 65:130–133.

U.S. Pat. Nos. 4,678,812 and 4,762,857 describe methods and compositions of tableting powders using the S-1 process of powder formation. These patents describe a process of forming an aqueous mixture of all the components of the finished tablet including trehalose, active ingredients, excipients, etc., spraying the aqueous mixture onto the surface of a moving bath of perfluorocarbon liquid, followed by lyophilization of the frozen droplets to dried powders. Trehalose is also described for use as a desiccant in food products, cosmetics and pharmaceuticals. EP publication nos. 606 753 A2; and 636 693.

All references cited herein, both supra and infra, are hereby incorporated herein by reference.

DISCLOSURE OF THE INVENTION

It has now been found that rapidly soluble (RS) tablets can be formed by adding a volatile salt to the tableting components, mixing the components to obtain a substantially homogeneous mixture, tableting the mixture and volatilizing the volatile salt. Any diluent or other tableting component known in the art can be used in formulating the RS tablets provided that an amount of binder sufficient to provide acceptable hardness is added. Additionally, it has now been found that trehalose, in a variety of physical forms, can be used to produce RS tablets of high quality. Unlike lactose, trehalose does not undergo chemical reactions, typical of the Maillard reaction, with amino, amine or amido groups. The anhydrous forms of trehalose also have been found to stabilize active agents that are sensitive to moisture. Thus, where stabilizing against the Maillard reaction and/or moisture is required, trehalose is the preferred diluent. Further, it has also been found that the amorphous forms of trehalose are preferred in tableting and produce tablets of very high quality and homogeneity.

The invention includes methods of producing RS tablets from various physical forms of powdered trehalose and combinations thereof. The forms of trehalose include, trehalose dihydrate (TD), which is in crystalline form, amorphous trehalose (AT), which is in vitreous form, and the anhydrous forms of trehalose, anhydrous amorphous trehalose (AAT) and anhydrous crystalline trehalose (ACT). The anhydrous trehalose powders (AAT and ACT) may contain AAT, and/or ACT. As used herein, "trehalose" refers to any physical form of trehalose including anhydrous, partially hydrated, fully hydrated and mixtures and solutions thereof.

As used herein, anhydrous trehalose refers to any physical form of trehalose containing less than about 2 percent water. The anhydrous forms of trehalose may contain from about 0–2% water and still retain superior properties in tableting. Amorphous trehalose (AT) contains about 2–9% water and TD contains about 9–10% water. The invention encompasses tablets formed with or without a disintegrant. The tablets including disintegrants have been found to dissolve rapidly and completely to form an aqueous solution of the active agent.

The invention encompasses methods of making tablets with increased dissolution rates. These rapidly soluble (RS) tablets are made by combining the diluent in powder form, an effective amount of active agent, a volatile salt, an amount of a binder sufficient to impart the required hardness to the finished tablet and any other excipients; and forming tablets from the mixture. The tablets are then exposed to a vacuum for a time and under conditions sufficient to substantially volatilize the volatile salt. The tablet thus obtained has increased surface area, decreased weight and increased dissolution rate compared to solid tablets of like dimensions. The tablets thus formed are also encompassed by the invention.

The invention also encompasses RS tablets composed of various ratios of AT, TD, AAT and/or ACT optionally including other tableting excipients. Different formulations of these components result in RS tablets with a wide variety of properties suitable for use with a number of varying types of active agents.

MODES FOR CARRYING OUT THE INVENTION

The invention encompasses methods of making RS tablets and compositions thereof. In a co-formulation of diluent and a volatile salt, such as ammonium bicarbonate, highly porous, rapidly dissolving tablets are produced on removal of the volatile salt. These tablets instantaneously disintegrate and dissolve on the tongue or into solution. Suitable volatile salts include, but are not limited to, ammonium bicarbonate, ammonium acetate and ammonium carbonate. The volatile salt can be incorporated to comprise up to about 50% (w/w) of the tablet. Preferably, the volatile salt is incorporated to comprise 30–50% (w/w) of the tablet.

The methods of making the RS tablets comprises thoroughly mixing, in powder form, a binder, preferably, trehalose, active agent, volatile salt, a sufficient amount of an additional binder to produce a tablet of suitable hardness and any other excipients and formed into a tablet by any method known in the art. After formation of the tablet, the salt is volatilized from the tablet by exposing the tablet to reduced atmospheric pressure for a time and under conditions sufficient to substantially completely remove the salt. For instance, in the case of ammonium bicarbonate, vacuum drying at 1.5 Torr at 60° C. for two hours was determined to be sufficient to remove the salt from a 3 mm thick tablet (see, Example 1). Although the optimal conditions must be determined empirically depending on the exact tablet components, it is well within the skill of one in the art, given the instructions herein, to make this determination. The resulting RS tablet has a decreased weight (up to 50%) compared to other tablets of similar size.

Unlike the seemingly similar "effervescent" tablets, however, the claimed RS tablets can be exposed to humidity without dissolving. Thus, the production, handling and packaging can be performed under ambient conditions, which is not possible with effervescent tablets, while retaining the light weight and rapid solubility inherent in effervescent tablets. Also, unlike effervescent tablets, these porous tablets do not release carbon dioxide in the presence of water and are thus suitable for chewable tablets. Due to the increased surface area of the porous tablets, they are not as hard as the solid tablets. In order to decrease friability of these tablets, an effective amount of an additional binder is added during processing. Any suitable binder may be used provided it is compatible with the active agent. The effective amount of binder can be determined empirically given the instructions herein. For instance 2–5% Ludipress or Kollidon was found to be effective.

In addition to the active agent, tablets may contain a variety of other components or "excipients." Diluents, typically powders, add bulk to make the tablet a practical size for compression. In compressed tablet formation, the dry components are mixed thoroughly, treated to produce a more homogeneous mixture and then compressed into tablets. For instance, in producing Phenobarbital tablets, dried Phenobarbital sodium, lactose, starch, talc and magnesium stearate (65, 26, 20, 20 and 0.3 mg each, respectively, per tablet) are thoroughly mixed. The mixture is then compressed into slugs. The slugs are ground and screened to 14 to 16-mesh granules. The granules are then recompressed into the final tablet. Although energy consumptive, these steps are necessary to assure the most homogeneous distribution possible.

Lactose is the most frequently studied tableting excipient, particularly spray dried lactose. Spray dried lactose contains about 15% anhydrous lactose. Pure amorphous lactose does not produce tablets as it lacks the plasticity imparted by the crystalline lactose. Thus, amorphous lactose must be mixed with crystalline lactose in order to produce tablets. The greater the concentration of amorphous lactose, the longer the dissolution time. This is because amorphous lactose does not disintegrate but, rather, dissolves from the surface. Increasing amounts of amorphous lactose also impart unacceptable hardness to tablets. Further, lactose reacts with amino groups via the Maillard reaction. Thus, lactose is unsuitable for use where the active agent or any excipients contain labile amino groups. With the increased use of peptides and peptide mimetics, for instance in oral tolerization regimens, lactose would be unsuitable as an excipient.

It has now been found that the use of trehalose produces tablets of superior qualities by all parameters tested. Unlike amorphous lactose, tablets made from AT do not suffer from excess hardness and readily dissolve under the appropriate conditions. In addition, trehalose, as a non-reducing sugar, does not react with amino groups, and its surprising resistance to hydrolysis to yield reducing sugars enables its use where the active agent or any excipients contain labile amino groups. Importantly, as demonstrated in the examples presented herein, in addition to producing tablets of superior physical properties, trehalose, and particularly AAT, provide increased stability of the active agent incorporated into the tablet and anhydrous trehalose further provides protection of the active agent from ambient humidity. Although TD also forms tablets, it can decrease the stability of moisture-sensitive and hygroscopic active agents; however, inclusion of anhydrous trehalose in the tablets can alleviate this problem. Without being bound by any one theory, applicants believe that the protection from humidity offered by anhydrous trehalose is due to its absorption of water molecules to produce TD and that this sequestration of the atmospheric water molecules from the active agents decreases the exposure of the active agent to moisture.

While any diluent known in the art is suitable for use herein, the use of anhydrous trehalose as a diluent in tablets imparts improved physical properties compared to prior art diluents. For instance, the active agents are more stable, in the case of AAT, the tablets are more resistant to humidity. In the following examples, anhydrous trehalose shows clear superiority over TD in maintaining the stability of an active agent.

Although singular forms may be used herein, more than one active agent and more than one excipient may be present in the compositions described and claimed herein. Determination of the types and effective amounts of these components is within the skill of one in the art.

The tablets may also be formed by combining effective amounts of diluent, active agent and excipients if any, in the powder form, processing the powder to form a substantially homogeneous mixture and forming tablets from the mixture. The diluent, if trehalose, can be TD, AT, AAT, ACT or mixtures thereof. The trehalose can initially be TD and can then be processed as described below to obtain the other physical forms. As described below, the processing step can be such that the powdered trehalose is in the form of TD, AT, AAT, ACT or mixtures thereof (one or more of these forms).

The diluent may also be ACT and/or AAT in any ratio and the compositions obtained thereby. The two anhydrous forms of trehalose may be mixed in a wide variety of ratios to obtain tablets of varying properties. TD and/or AT and/or any other diluents may also be incorporated to impart desired characteristics of hardness, friability and dissolution times. The anhydrous trehalose mixtures can be obtained according to the methods described herein or by any other method known in the art. The components, diluent, active agent, binders, volatile salt and excipients, if any, are combined, mixed, and formulated into tablets by any method known in the art.

The tablets may further comprise AT as a diluent. As used herein, AT is non-crystalline or "vitreous" trehalose containing water in an amount greater than 2% (anhydrous) but less than 10% (fully hydrated). AT imparts stability on active agents dried therein and thus dry solid trehalose formulations containing active agents can readily be tableted with any other form of trehalose as a totally compatible tableting excipient. If the AT formulation produced is dried sufficiently to yield at least a mixture of anhydrous trehalose and AT, the dry solid formulation containing the active agent can be used directly in tableting without the use of additional anhydrous trehalose as a tableting excipient. Although this would be more energy consuming, it would yield the advantage of a homogeneously distributed active agent at a molecular level within the tablet which may be desirable under certain circumstances.

Any tableting aids, or excipients, known in the art can be included in the formulations. Excipients other than diluents include, but are not limited to, binders, lubricants, disintegrants, coloring agents and flavoring agents.

Binders, or granulators, impart cohesive qualities to the powdered material. Suitable binders include any known in the art, including, but not limited to starch, gelatin and sugars such as sucrose, glucose, dextrose, molasses and lactose. Natural and synthetic gums that are also suitable, include, but are not limited to, acacia, sodium, alginate, extracts of Irish moss, panwar gum, ghatti gum, mucilage of isapol husks, carboxymethylcellulose etc. Any other suitable binders known in the art may be added including, but not limited to, Ludipress, Kollidon, polyvinyl pyrolidone (PVP) and HES. Kollidon is sold as Kollidon VA64 (BASF) and is a polyvinyl pyrolidone based binder. Ludipress (BASF) is a commercial tableting mixture of primarily lactose and PVP. Byco A (Croda) is degraded gelatin of 2500–4000M. Wt. range. HES (NPBI) is hydroxyethyl starch. As discussed below, under certain conditions, the addition of binders is necessary to achieve the correct degree of hardness in the RS tablets.

Lubricants are used for a number of purposes, including preventing adhesion of the blended materials to the surface of the die and punch, reducing interparticle friction, facilitating the ejection of the tablets from the die cavity and improving the flow of the tablet granulation.

In the examples presented herein, magnesium stearate was routinely used as a lubricant, and is the preferred lubricant. Any other suitable lubricant known in the art may be used including, but not limited to, talc, calcium stearate, stearic acid, hydrogenated vegetable oil, lutrol and polyethylene glycol (PEG). Disintegrants are added to facilitate breakup or disintegration of the tablet before or after administration. Coloring agents make the dosage form more esthetic in appearance and may serve as identification. Flavoring agents are usually added to provide sweetness to chewable or dissolvable tablets. The invention encompasses tablets formed from trehalose with or without any excipient or any suitable combinations of excipients.

The active agent can be any known in the tableting art and is typically a pharmaceutical agent, biological modifier, or diagnostic component. Pharmaceutical agents include, but are not limited to, antipyretic and antiinflammatory drugs, analgesics, antiarthritic drugs, antispasmodics, antidepressants, antipsychotics, tranquilizers, antianxiety drugs, narcotic antagonists, antiparkinsonism agents, cholinergic agonists, chemotherapeutic drugs, immunosuppressive agents, antiviral agents, antibiotic agents, parasiticides, appetite suppressants, antiemetics, anticholinergics, antihistaminics, antimigraine agents, coronary, cerebral or peripheral vasodilators, hormonal agents, contraceptives, antithrombotic agents, diuretics, antihypertensive agents, cardiovascular drugs, opioids and vitamins. Detailed parameters and discussions of such active agents can be found, for instance, in the Physician's Desk Reference (1995) 49th ed., Medical Economics Data Production Co. New Jersey. An amount of active agent is used such that there is an "effective amount" in each tablet formed. An effective amount is thus a single unit dosage which may vary depending on whether the tablets are obtained over the counter or via prescription. For instance, Sudafed® brand nasal decongestant contains 30 mg pseudo-ephedrine hydrochloride per tablet when obtained over the counter and 60 mg per tablet when obtained via prescription.

The chemical structures of such active agents, include, but are not limited to, lipids, organics, proteins, synthetic peptides, natural peptides, peptide mimetics, peptide hormones, steroid hormones, D amino acid polymers, L amino acid polymers, oligosaccharides, polysaccharides, nucleotides, oligonucleotides, nucleic acids, protein-nucleic acid hybrids, antigens and small molecules. Suitable proteins include, but are not limited to, enzymes, biopharmaceuticals, growth hormones, growth factors, insulin, monoclonal antibodies, interferons, interleukins, collagen and cytokines. Suitable organics include, but are not limited to, vitamins, neurotransmitters, antimicrobials, antihistamines, analgesics and immunosuppressants. Suitable steroid hormones include, but are not limited to, corticosteroids, estrogen, progesterone, testosterone and physiologically active analogs thereof. Suitable nucleic acids include, but are not limited to, DNA, RNA and physiologically active analogs thereof.

Active agents commonly used in diagnostics include, but are not limited to, dyes, antibodies, enzymes, hormones and antibiotics.

Any other tableting methods or formulations known in the art can also be used. For instance, the invention encompasses coated tablets, chewable tablets, effervescent tablets, molded tablets or tablet triturates, encapsulated tablets, microencapsulated tablets and sustained release tablets. The tablets produced are suitable for use in any animal including humans. Although the tablets described herein are for human use, suitable veterinary formulations are readily fashioned given the skill of one in the art and the Examples and Description presented herein.

The following examples are provided to illustrate, but not limit, the claimed invention. Powders used in tableting must have excellent flow properties and consistent particle size. For the purposes of these trials, particle size was not stringently controlled, but powders were formulated to have flow characteristics suitable for tablet production. The flow characteristics obtained were found to enable loading the tablet die without difficulty. A sieving procedure can be incorporated to ensure a more even particle size. This is essential in larger batches to guarantee thorough mixing of the components and it is well within the skill of one in the art to devise a suitable sieving procedure.

EXAMPLE 1

RS Tablet Formulations

300 µl aliquots of a solution of 43.4 mg/ml trehalose containing 66 mg/ml of an antimicrobial peptide was dried in 10 ml polypropylene tubes (10 mm diameter) in the FTS drier. Samples, at 25° C., were loaded onto a shelf in the drier that had been preheated to 35° C. The vacuum pressure in the chamber was progressively reduced to 20 Torr over 10 minutes. This pressure was held for a further 30 minutes before the pressure was further reduced to 30 mTorr. After 17 hours, the shelf temperature was increased to 50° C. This shelf temperature was maintained for 3 hours after which the cycle was stopped. The amorphous trehalose (AT) matrix produced contained the active in solid solution in a foamed trehalose glass (FTG) and had an open plug-like structure similar to freeze-dried materials. Moisture content was typically 1.1 to 2% (w/w). The DSC trace of a typical sample with water content of 1.59% shows a glass transition of 83°–84° C. characteristic of the amorphous form of trehalose.

The FTGs formed were ground to a fine powder in a Waring blender in a controlled environment of 15% relative humidity (RH), before being used in the tableting formulations. All the tableting components were then thoroughly mixed in a 20 ml glass vial and aliquots of 0.5 g of powder were weighed out into a 0.5 inch Manesty type die. The tablet was formed by hammering onto the upper punch with a single light positioning blow, followed by a stronger single blow. The tablets were of a convex oval shape and at least 3 mm thick. On release from the die, the tablets were stored in sealed vials or, in the case of formulations containing ammonium bicarbonate, subjected to vacuum drying at 1.5 Torr and 60° C. for two hours for removal of the volatile salt. Duplicate sets of the tablets containing ammonium bicarbonate were made, one set was subject to vacuum to remove the volatile salt and the other set was not treated further. Disintegration and dissolution of the tablets was studied in aqueous solution with gentle agitation and not stirred. The compositions and results obtained for tableting are presented in Table 1. Table 2 depicts the effect of volatile salt removal on various physical characteristics of the tablets. These results are presented as disintegration time in minutes (Distgn), and dissolution time in minutes (Dissln), of the tablets containing volatile salts. Disintegration is defined as the break up of the tablet into fragments of different sizes. Dissolution is defined as total dissolution and "no dis" indicates no disintegration. In Table 1, sample 1 is an example of tablets produced using AAT produced by spray drying. All other examples use AAT produced as FTG. In Table 1 amm. bicarb. stands for ammonium bicarbonate, L stands for Ludipress and Mg Stearate is present as a binder. As Ludipress is a mixture of 93% lactose monohydrate and 6% Kollidon. Thus in some formulations, such as blend 1, lactose was the major tableting excipient in the RS tablets produced and no difference in the quality or properties of the tablets were observed with the use of different excipients for the formation of RS tablets.

TABLE 1

| Sample | Composition (Wt %) | | | | |
|---|---|---|---|---|---|
| | Trehalose glass | Binder | Amm. bicarb. | Mg Stearate | Comments |
| 1 | 30 | L 39.5 | 30 | 0.5 | Good tablets formed |
| 2 | 56 | L 13.5 | 30 | 0.5 | Good tablets formed |
| 3 | 80 | L 19.5 | — | 0.5 | Good tablets formed. |
| 4 | 42.5 | L 40 | 16.5 | 1.0 | Good tablets formed. |
| 5 | 39.2 | L 30.8 | 29.5 | 0.5 | Good tablets formed |
| 6 | 44 | L 26 | 29.5 | 0.5 | Good tablets formed. |
| 7 | 38.8 | HES 30.7 | 30 | 0.5 | Good tablets formed. |
| 8 | 51.2 | HES 18.3 | 30 | 0.5 | Good tablets formed. |

TABLE 2

| | Before vac. drying | | After vac. drying | | |
|---|---|---|---|---|---|
| Sample. | Distgn. | Dissln. | Distgn. | Dissln | Comments |
| 1 | no dis. | 12 | 2.5 | 6 | Gradual surface dissolution. Disintegrates after vacuum. |
| 2 | n/d | n/d | 0.5 | 5 | Good porous tablet |
| 3 | n/d | n/d | n/d | n/d | |
| 4 | 3 | 11–12 | 1 | 4 | |
| 5 | no dis. | 9 | 1.5 | 7 | |
| 6 | 3.5 | 4.5 | 1.26 | 2 | |
| 7 | 2 | 6.5 | 0.2 | 1.5 | Rapid disintegration. |
| 8 | no dis. | 9–10 | 0.2 | 2 | Rapid dissolution. |

The results summarized in Tables 1 and 2 indicate that AAT produced from either FTGs or spray dried formulations, formed good tablets. Tablets formed using formulations containing volatile salt showed enhanced dissolution rates after removal of the volatile salt from the tablets under vacuum. Up to 50% (w/w) of the volatile salt can be incorporated into the tablet with the use of suitable binders. Generally, the FTGs gave better tablets than the spray dried formulations but this was dependent on the exact tableting mix used. These results also indicate that various binders are suitable for use in the RS tablets. Though the results for only magnesium stearate are included other lubricants such as sodium benzoate have also been shown to be suitable for use. Thus, any lubricant is also suitable for use in the tablets formed using AAT.

EXAMPLE 2

Use of AAT and ACT in Tablet Production

The following example utilizes the amorphous and crystalline forms of anhydrous trehalose, for the production of tablets. The anhydrous trehalose was manufactured by heating crystalline TD at 60° C., at atmospheric pressures to obtain ACT or under vacuum with heat to obtain the AAT. Crystalline TD was incubated in open trays at temperatures of 55° C., 70° C. and 80° C. in a standard laboratory oven for 24–72 hours. Samples were assayed for water content by Karl Fischer analysis and selected samples were also analyzed by DSC. Surprisingly, the samples all showed water contents ranging from 0.1–2%, even those heated at just 55° C. The DSC trace of a sample heated at 70° C. for 48 hours showed a crystalline melt at approximately 210°–216° C. characteristic of the melting temperature of ACT. The water content of the sample was 0.33%. This endotherm is distinct from the melt endotherm at the lower temperature of 96°–101° C. characteristic of TD seen in the DSC analysis of crystalline dihydrate.

Crystalline TD was incubated in open trays for 16–24 hours in either a Heraus vacuum oven with a reduced pressure of 1.5 Torr, or in a FTS freeze drier with a reduced pressure of 30 mTorr, and the shelf temperature set at 60° C. Samples were again assayed for water content by Karl Fischer analysis and selected samples were also analyzed by DSC. Samples typically showed water contents lower than those in described above, ranging from 0.1–1.5%. The DSC trace of a sample heated at 60° C. for 24 hours in a vacuum oven at 1.5 Torr no longer showed a crystalline melt at approximately 215° C., but instead showed a glass transition at 116°–117° C. characteristic of the amorphous form of trehalose demonstrating the formation of AAT. The water content of the sample was below 0.1%.

The blends used in the tableting of anhydrous trehalose contained either single forms of anhydrous trehalose or mixtures thereof, and also optionally contained a number of commercially used binders such as Kollidon VA64, Ludipress, BycoA and HES and lubricants such as magnesium stearate, sodium lauryl sulfate and Lutrol.

The production of rapidly dissolving tablets was again achieved by the addition of a volatile salt to the tableting blend followed by the removal of the salt under vacuum to obtain a porous tablet that showed increased dissolution rates compared to tablets of the same blends without the volatile salt incorporated. Aliquots of 0.5 g of powder were weighed out into a 0.5 inch Manesty type die. The tablet was formed by hammering onto the upper punch (A single light positioning blow, followed by a stronger single blow). The tablets were of a convex oval shape and at least 3 mm thick. On release from the die, the tablets were stored in sealed vials. In tablets formed from blends containing ammonium bicarbonate, the volatile salt was removed under a vacuum of 1.5 Torr at 60° C. for six hours to yield porous, rapidly dissolving tablets which were again stored in sealed vials prior to analysis. Disintegration and dissolution of the tablets was studied in distilled water at 28° C. with gentle agitation.

The results obtained on tableting the various blends of anhydrous trehalose and disintegration and dissolution are presented in Tables 3 and 4 respectively. In Table 3, * stands for anhydrous trehalose, K stands for Kollidon and B stands for BycoA. Table 4 shows the effect of increased porosity on rate of disintegration/dissolution of selected tablets. Similar results were obtained for the formation of tablets from these formulations using the automated Manesty F3 tableting press.

TABLE 3

| | Composition (Wt %) | | | | |
|---|---|---|---|---|---|
| Sample | Trehalose form | Tab. aid | Amm. bicarb. | Mg stearate | Comments |
| 1 | 99.5 AAT | — | — | 0.5 | Good |
| 2 | 69.5 AAT | — | 30 | 0.5 | Good |
| 3 | 59.5* | — | 40 | 0.5 | Some lamination |
| 4 | 49.5* | — | 50 | 0.5 | Occasional lamination |
| 5 | 64.97 ACT | HES 4.8 | 29.6 | 0.53 | Excellent |
| 6 | 39.5* | B 10 | 50 | 0.5 | Mostly good |
| 7 | 44.5%* | B 5 | 50 | 0.5 | Good. Few laminate after storage |
| 8 | 69.5* | — | 30 | 0.5 | Excellent |
| 9 | 67.5* | B 2 | 30 | 0.5 | Good |
| 10 | 50* | — | 50 | — | Excellent |
| 11 | 55* | K 5 | 40 | — | Excellent |
| 12 | 54.5* | K 5 | 40 | 0.5 | Excellent |

TABLE 4

| Sample | Disint | Dissol | Comments |
|---|---|---|---|
| 5 | — | 7.5 mins | no disintegration |
| 6 | — | 1 min | — |
| 7 | 15 secs | 45 secs | most dissolves in 30 secs |
| 8 | — | 4 mins | no disintegration |
| 9 | — | 2 mins | no disintegration |
| 10 | 10 secs | 45 secs | — |
| 11 | 15 secs | 1 min | — |
| 12 | 10 secs | 1 min | — |

The results presented in Table 4 indicate that removal of volatile salt to give porous tablets significantly increased the disintegration and dissolution rates of the tablets produced. Complete removal of the volatile salt was assessed by difference in tablet weight before and after vacuum treatment. AT compresses better than FTG, and volatile salt can be incorporated in up to at least 50 weight %. This leads to a highly porous matrix after the volatile salt has been removed. AT alone remains a good binder, though some loss in intrinsic strength is seen in tablets of blends incorporating ammonium bicarbonate and especially once the volatile salt has been removed. Without a binder of some kind, these porous tablets are very fragile and a balance is therefore essential between a high proportion of volatile and inclusion of a small percentage of binder. These porous tablets dissolve rapidly when compared to tablets formed from trehalose alone; the time for full dissolution is generally reduced from 10–15 minutes down to less than 1 minute.

Although the foregoing invention has been described in some detail by way of illustration and example for purposes of clarity and understanding, it will be apparent to those skilled in the art that certain changes and modifications may be practice. Therefore, the description and examples should not be construed as limiting the scope of the invention which is delineated by the appended claims.

We claim:

1. A method of making rapidly soluble tablets comprising the steps of:
   a) combining, in substantially dry form, components comprising a diluent, an amount of binder sufficient to increase the hardness of the tablets formed to acceptable levels; an amount of an active agent such that each tablet formed contains an effective amount of the active agent, and an amount of volatile salt effective to decrease the weight and increase the surface area of the tablet formed volatilized;
   b) processing the product of step a) to form a substantially homogeneous mixture;
   c) forming tablets from the mixture of step b); and
   d) volatilizing the volatile salt from the tablets.

2. The method according to claim 1, wherein the diluent is trehalose, dicalcium phosphate, dihydrate, calcium, tricalcium, phosphate, sulfate, lactose, spray-dried lactose, pregelatinized starch, microcrystalline cellulose, cellulose, kaolin, mannitol, sodium chloride, dry starch or powdered sugar.

3. The method according to claim 2, wherein the trehalose is trehalose dihydrate, amorphous trehalose, anhydrous amorphous trehalose, anhydrous crystalline trehalose or mixtures thereof.

4. The method according to claim 1, wherein the components of step a) further comprise at least one excipient.

5. The method according to claim 4, wherein the excipients are diluents, lubricants, disintegrants, coloring agents or flavoring agents.

6. The method according to claim 5, wherein the lubricant is talc, calcium stearate, stearic acid, hydrogenated vegetable oil, lutrol, polyethylene glycol or magnesium stearate.

7. The method according to claim 1, wherein the binder is starch, gelatin, sugars, natural and synthetic gums, Ludipress, Kollidon, polyvinyl pyrolidone or hydroxyethyl starch.

8. The method according to claim 1, wherein step d) comprises exposing the tablet to reduced pressure for a time sufficient to volatilize the volatile salt.

9. The method according to claim 8, wherein the pressure is about 0.5–30,000 mTorr for 0.5–6 hr.

10. The method according to claim 1 wherein the active agent is antipyretic drugs, anti-inflammatory drugs, analgesics, antiarthritic drugs, antispasmodics, antidepressants, antipsychotics, tranquilizers, antianxiety drugs, narcotic antagonists, antiparkinsonism agents, cholinergic agonists, chemotherapeutic drugs, immunosuppressive agents, antiviral agents, antibiotic agents, parasiticides appetite suppressants, antiemetics, anticholinergics, antihistaminics, antimigraine agents, coronary vasodilators, cerebral vasodilators, peripheral vasodilators, hormonal agents, contraceptives, antithrombotic agents, diuretics, antihypertensive agents, cardiovascular drugs, opioids, or vitamins.

11. The method of claim 1 wherein the volatile salt is selected from the group consisting of ammonium bicarbonate, ammonium acetate and ammonium carbonate.

12. A composition comprising a tablet formulation according to the method of any of claims 1–10 or 11.

* * * * *